(12) United States Patent
Butler et al.

(10) Patent No.: US 8,092,785 B2
(45) Date of Patent: Jan. 10, 2012

(54) PROCESS FOR MILLING POORLY SOLUBLE DRUGS IN PRESENCE OF LIQUID PROPELLANTS

(75) Inventors: James Matthew Butler, Harlow (GB); Angus Harry Forster, Stevenage (GB); James Edon Patterson, Harlow (GB); John Peter Warr, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1004 days.

(21) Appl. No.: 11/574,083

(22) PCT Filed: Aug. 22, 2005

(86) PCT No.: PCT/GB2005/003269
§ 371 (c)(1),
(2), (4) Date: Feb. 4, 2008

(87) PCT Pub. No.: WO2006/021768
PCT Pub. Date: Mar. 2, 2006

(65) Prior Publication Data
US 2008/0260657 A1    Oct. 23, 2008

(30) Foreign Application Priority Data
Aug. 23, 2004 (GB) .................................. 0418791.0

(51) Int. Cl.
A61K 9/00 (2006.01)
A61K 9/12 (2006.01)
A61K 9/14 (2006.01)
(52) U.S. Cl. .......................................... 424/46; 424/489
(58) Field of Classification Search .................. 424/489, 424/45
See application file for complete search history.

(56) References Cited

U.S. PATENT DOCUMENTS

| 5,711,934 A | 1/1998 | Adjei et al. |
| 6,613,307 B1 * | 9/2003 | Cooper ............................. 424/45 |
| 2002/0003179 A1 | 1/2002 | Verhoff et al. |
| 2004/0037785 A1 | 2/2004 | Staniforth et al. |
| 2005/0085445 A1 * | 4/2005 | Muller et al. .................... 514/58 |
| 2008/0279949 A1 * | 11/2008 | Merisko-Liversidge et al. ............................. 424/489 |

FOREIGN PATENT DOCUMENTS

| EP | 0 499 299 A2 | 8/1992 |
| WO | WO 93/25190 A1 | 12/1993 |
| WO | 00/27363 | 5/2000 |
| WO | 00/57881 | 10/2000 |
| WO | 02/43701 | 6/2002 |
| WO | 02/094443 | 11/2002 |
| WO | WO 02/089773 A2 | 11/2002 |
| WO | WO 03/066031 A1 * | 8/2003 |
| WO | WO 2005/053851 | 6/2005 |

OTHER PUBLICATIONS

Mura, et al. *Drug Development and Industrial Pharmacy*, 27(2): 119-128 (2001).
Brittain. *Journal of Pharmaceutical Sciences*, 91(7): 1573-1580 (2002).
Boldyrcv, et al. *Drug Development and Industrial Pharmacy*, 20(6): 1103-1113 (1994).
Huttenrauch, et al. *Pharmaceutical Research*, 2: 302-306 (1985).
Matsumoto, et al. *Pharmaceutical Research*, 16(11): 1722-1728 (1999).
Otsuka, et al. *Chem. Pharm. Bull (Tokyo )*, 34(4): 1784-1893 (1986).
Crowley, et al. *Journal of Pharmaceutical Sciences*, 91(2): 492-507 (2002).
Geze, et al. *International Journal of Pharmaceutics*, 178(2): 257-268 (1999).
Mura, et al. *Journal of Pharmaceutical and Biomedical Analysis*, 30(2): 227-237 (2002).
Lizio, et al. *AAPS PharmSciTech*, 2(3): Article 12 (2001).
Amidon, et al. *Pharmaceutical Research*, 12(3): 413-420 (1995).
Galia, et al. *Pharmaceutical Research*, 15: 698-705 (1998).

* cited by examiner

*Primary Examiner* — James H. Alstrum-Acevedo
(74) *Attorney, Agent, or Firm* — Dara L. Dinner; Theodore R. Furman (57) ABSTRACT

Drug substance for use in a pharmaceutical formulation may be prepared by a process which process comprises co-milling a suspension of the drug substance and a pharmaceutically acceptable polymer in a liquid propellant.

18 Claims, 6 Drawing Sheets

1    Diaphragm pump
2    Getzmann mill

Figure 3

PROCESS FOR MILLING POORLY SOLUBLE DRUGS IN PRESENCE OF LIQUID PROPELLANTS

This application is a National Stage Application filed under 35 U.S.C. §371 of PCT/GB2005/003269.

FIELD OF THE INVENTION

The present invention relates to a novel process for preparing drug substance for use in a pharmaceutical formulation.

BACKGROUND OF THE INVENTION

It is often found necessary to process bulk drug substance to improve its properties prior to further processing into final product form. Options include melt-extrusion, spray drying and various types of milling. This may be for one or more of several reasons, for instance, to improve processability or to improve bioavailability.

It is often found helpful to subject poorly soluble compounds to milling, either by a dry process such as micronisation, or in the presence of a liquid (typically aqueous), to decrease particle size, thereby improving the dissolution rate and bioavailability of the compound by increasing the surface area (Mura et al, 2001, *Drug Development and Industrial Pharmacy* 27 (2): 119-128). Such milling however requires a significant amount of energy and this can lead to unwanted solid state transitions such as a polymorphic conversion or amorphous formation (Brittain, 2002, *Journal of Pharmaceutical Sciences* 91 (7): 1573-1580). In some instances, however, it may be useful to deliberately induce amorphous form conversion, not only of neat drug substance but also drug:polymer blends, see for instance the work of Boldyrev et al (1994, *Drug Development and Industrial Pharmacy* 20 (6): 1103-1113) on ball milling of sulfathiazole and PVP which resulted in the formation of a glass solution. Prolonged milling can result in the drug substance absorbing the excess free enthalpy and this can lead to an acceleration not only of physical reactions but also of undesirable chemical reactions (Huttenrauch et al, 1985, *Pharmaceutical Research* 2: 302-306).

There are a number of process variables involved in a milling process which can influence the physical form of the product such as temperature, grinding media, frequency and duration. Thus, the temperature at which milling is performed has been shown to influence the physical form of the final milled product. Milling of a drug:polymer system under dry conditions results in significant generation of heat. Masumoto et al (1988, *Pharmaceutical Research* 16 (11): 1722-1728) ball milled phenylbutazone at different temperatures (4° C. and 35° C.). Milling temperature was reported to influence the polymorphic form of the final product. Otsuka et al (1986, Chem Pharm Bull (Tokyo). 34 (4):1784-93) found that milling temperature (4° C. and 30° C.) influenced the duration of milling required to convert the $\alpha$ and $\gamma$ indomethacin polymorphs to the amorphous form. Crowley and Zografi (2002, *Journal of Pharmaceutical Sciences* 91 (2): 492-507) showed that ball milling indomethacin in a vessel submerged in liquid nitrogen (cryogenic impact mill) resulted in amorphous conversion. Ball milling has also been carried out with liquid nitrogen in direct contact with the drug substance (Geze et al, 1999, *International Journal of Pharmaceutics* 178 (2): 257-268).

The physical state of the milled product is also influenced by formulation variables. Thus, the addition of amorphous polymers such as PVP can increase the amorphous conversion of a compound. Mura et al (2002, *Journal of Pharmaceutical and Biomedical Analysis* 30 (2): 227-237) found that when glisentide was milled with PVP, the time and frequency of milling necessary to obtain an amorphous product was decreased. Boldyrev et al (1994) found that increasing the proportion of PVP and milling resulted in a decrease in crystalline nature of the product.

An aspect of milling in the presence of a liquid (typically aqueous), is the need to recover and then dry the resultant milled drug substance from the suspension. Filtration is often difficult. Spray drying may be used to avoid these problems, but efficient isolation of the very fine particles may still be difficult. In addition, spray drying on a large scale requires substantial capital investment, is energy intensive and produces large volumes of solvent which have to be dealt with.

Ball milling at low temperatures has been reported. Thus, for instance, Geze et al (ibid) milled 5-iodo-2'-deoxyuridine in the presence of liquid nitrogen in the sample vessel, resulting in decreased mean particle size and narrower particle size distribution.

Lizio et al (AAPS PharmSciTech 2001, 2 (3), article 12) describe the low temperature micronisation of a peptide drug in a fluid propellant (heptafluoropropane) in a modified pearlmill coupled to a cryostat, at temperatures of −50 and −90 deg C.

WO2005/053851 (E I DuPont De Nemours and Company, published 16 Jun. 2005, after the priority date of the present application) describes a high pressure media milling system and process of milling particles, to provide fine and ultra-fine particles.

The main focus is milling in supercritical carbon dioxide. Example 3 however describes the media milling of lactose crystals in a pressurised pharmaceutical propellant, HFC-134a, in the presence of a surfactant, sorbitan mono-oleate. There is however no discussion on the physical form of the resultant milled material.

It has now been found that co-milling in a liquid propellant in the presence of a pharmaceutically acceptable polymer can have a beneficial influence on the physical state of the drug substance in the milled product, in particular in promoting the crystalline form of the drug substance, rather than the amorphous form, as might otherwise have been predicted.

BRIEF DESCRIPTION OF THE DRAWINGS

FIG. 1.1 (top to bottom) demonstrates an XRPD of carbamazepine 134 milled, carbamazepine milled, carbamazepine:PVP/VA 37 milled, carbamazepine:PVP/VA 64 milled, carbamazepine:PVP 134a milled and carbamazepine: PVP milled.

FIG. 1.2 (top to bottom) demonstrates an XRPD of dipyridamole 134a milled, dipyridamole:PVP 134a milled, dipyridamole milled and dipyridamole:PVP milled.

FIG. 1.3 (top to bottom) demonstrates an XRPD of glibenclamide 134a milled, glibenclamide:PVP 134a milled, glibenclamide milled and glibenclamide:PVP milled.

FIG. 1.4 (top to bottom) demonstrates an XRPD of indomethacin 134a milled, indomethacin:PVP 134a milled, indomethacin milled and indomethacin:PVP milled.

FIG. 1.5 (top to bottom) demonstrates an XRPD of the co-milled Compound A/HPMCAS sample and a physical blend of the two components.

FIG. 1.6: (top to bottom) demonstrates an XRPD for the co-milled Compound A/HPMC 33:67 sample and physical blend of the two components.

FIG. 2.1 demonstrates dissolution profiles of carbamazepine products prepared by ball milling and 134a ball milling (cabz=carbamazepine, PVP=polyvinyl-pyrrolidone, VA=vinyl acetate, 134a=propellant 134a)).

FIG. 2.2 demonstrates dissolution profiles of dipyridamole products prepared by ball milling and 134a ball milling (dipm=dipyridamole).

FIG. 2.3 demonstrates dissolution profiles of glibenclamide products prepared by ball milling and 134a ball milling (glb=glibenclamide).

FIG. 2.4 demonstrates dissolution profiles of indomethacin products prepared by ball milling and 134a ball milling (ind=indomethacin).

FIG. 2.5 demonstrates the dissolution profiles of Compound A formulations.

DETAILED DESCRIPTION OF THE INVENTION

Accordingly, the present invention provides a process for preparing a drug substance for use in a pharmaceutical formulation which process comprises co-milling a suspension of the drug substance and a pharmaceutically acceptable polymer in a liquid propellant.

As used herein, the pharmaceutically acceptable polymer may be a single polymer or a mixture or one or more polymers, for instance a mixture of two or three different polymers.

As used herein, "milling" (in "co-milling") refers to stirred media milling.

The milling process may be carried out in a conventional milling vessel, which is sealed to maintain the liquid propellant in liquid form, under pressure, and with no external control of temperature. It will be appreciated that the temperature inside the mill will however rise, due to the input of energy. Alternatively, the milling vessel may be cooled, for instance with a cryostat or cooling jacket, so that the low boiling liquid propellant is maintained in a liquid state. The co-milling process is carried at lower operating pressures than those typically used for carbon dioxide, for instances up to 15 bar, typically at about 3 to 8 bar.

It is found that drugs processed according to the present invention show a decreased tendency for conversion to amorphous form and may retain their crystalline form. A crystalline form is preferred for a drug substance as it can be more fully characterised and is easier to control than an amorphous form. Particle size, as measured by laser diffraction sizing, may also be reduced, beyond that which may be achieved with other techniques such as dry bead milling. Co-milling with a polymer is found to lead to a highly intimate physical blend, rather than an amorphous solid dispersion. This leads to improved solubility and/or dissolution rates. Furthermore, this form of co-milling eliminates the need for an extra drying step as the propellant is evaporated away at the end of the process, under ambient pressure, by lowering the pressure and/or raising the temperature, according to conventional practice.

The use of a liquid propellant rather than liquid carbon dioxide is advantageous as the equipment required is less expensive, as the process can be carried at lower operating pressures.

Drug substances which may benefit from the present invention include those in Classes II and IV according to the Biopharmaceutics Classification system (Amidon et al, *Pharmaceutical Research* 12 (3): 413-420, 1995) This classifies drug substances according to their solubility and permeability. Those in class II have low solubility and high permeability and where the rate limiting step for absorption is drug dissolution whilst those in class IV have low solubility and low permeability, so are poorly absorbed by the oral route. Co-milling according to the present invention provides drug substance with improved dissolution properties. Examples of Class II compounds include carbamazepine, dipyridamole, indomethacin and glibenclamide.

Liquid propellants for use in the present process include liquefied gases used in aerosols, for instance fluoro hydrocarbons and chlorfluoro hydrocarbons such as 1,1,1,2-tetrafluoroethane (propellant 134a), propellant 227 (heptafluoropropane), tricholorfluoromethane and dichlorodifluoromethane, and hydrocarbons such as propane and butane. For use in the present process, a sealed milling vessel is used and the propellant may be added in liquid form, to decrease the temperature and raise the pressure within the vessel. The process requires that the drug substance and polymer are present as a suspension in the liquid propellant. Whilst the drug substance will generally be essentially insoluble in the liquid propellant, polymers may be used which are essentially insoluble or have limited solubility.

Representative pharmaceutically acceptable polymers for use in the present invention include those conventionally used in co-milling, for instance hydrophilic amorphous polymers such as polyvinyl pyrrolidone (PVP), such as the grades K30 PVP, polyvinyl pyrrolidone/vinyl acetate (VA) co-polymers such as PVP/VA 64 and PVP/VA 37, and cellulose derivatives such as hydroxypropyl methylcellulose and polymers the solubility of which is pH dependent, for instance an enteric polymer such as hydroxypropyl methylcellulose acetate succinate. Further representative polymers include water soluble, preferably hydrophilic, polymers such as polyethylene glycols, block co-polymers such as poloxamer and cross-linked water insoluble polymers normally used in pharmaceutical formulations as disintegrants, such as crospovidone and croscarmellose sodium. The ratio of drug:polymer is in the range 2:1 to 1:10, preferably 2:1 to 1:5, typically about 1:1 or 1:2, by weight.

The weight (of drug substance and polymer) to volume (of milling vessel) ratio may be in the range 1 to 20%, preferably 1 to 10%, typically about 2%, for a non-recirculating system.

Typically, drug substance and polymer are present in from 1 to 30%, for instance 5 to 20% by weight of the liquid propellant.

In a further aspect, the present invention provides for a process for preparing a drug substance for use in a pharmaceutical formulation which process comprises co-milling a suspension of the drug substance in the presence of liquid 1,1,1,2-tetrafluoroethane in the presence of a pharmaceutically acceptable polymer such as polyvinylpyrrolidone.

In a further aspect, the present invention provides for a process for preparing a drug substance for use in a pharmaceutical formulation which process comprises co-milling a suspension of the drug substance in the presence of liquid propellant such as 1,1,1,2-tetrafluoroethane in the presence of a pharmaceutically acceptable cellulose derivative such as hydroxypropyl methylcellulose.

In a further aspect, the present invention provides for a process for preparing a drug substance for use in a pharmaceutical formulation which process comprises wet co-milling a suspension of the drug substance in the presence of liquid propellant such as 1,1,1,2-tetrafluoroethane in the presence of a pharmaceutically acceptable polymer the solubility of which is pH dependent, for instance an enteric polymer, such as hydroxypropyl methylcellulose acetate succinate.

In a further aspect, the present invention provides for a process for preparing an intimate admixture of a drug substance and a polymer which process comprises co-milling a suspension of the drug substance and the polymer in a liquid propellant.

In a further aspect, the present invention provides a process for obtaining a finely milled drug substance which process comprises co-milling a suspension of the drug substance in the presence of a polymer in a liquid propellant.

In a further aspect, the present invention provides a co-milling process for substantially retaining the crystallinity of the drug substance which process comprises co-milling a suspension of the crystalline drug substance in the presence of a polymer in a liquid propellant.

The milling process of the present invention may be carried out in a stirred media mill. Suitable such mills are well known in the art and available from commercial sources, for instance an MM2 Mixer mill (Glen Creston) and a Retsch MM200 Mixer mill, using milling balls appropriate to the size of the vessel. Suitable milling balls include (stainless) steel, ceramic and yttrium stabilised zirconium milling beads. Other suitable mills include a pearl mill, using glass or tungsten pearls, such as that described by Lizio et al (ibid). This particular mill is adapted for temperature control of the milling, being equipped with a cryostat. Milling conditions will be dictated by the nature of the materials and aim of the process, and may have one or more cycles, according to conventional criteria. Milling duration may be in the range of 30 to 150 minutes, and may consist of one or more cycles, for instance 120 minutes and 2×20 minutes.

For operation without external control of the temperature, the milling vessel is equipped with sealable closure so that it may be sealed during the milling operation, thereby ensuring that the liquid propellant is retained as a liquid, under pressure. It will be appreciated that is in such circumstances, the mill itself may warm up due to the action of the mill.

In larger scale operations, it may be beneficial to provide the milling vessel with a cooling jacket, so that the temperature within the milling vessel may be controlled and any excessive increase in operating temperatures avoided.

In larger scale operations, the milling chamber may be supplied with a suspension of drug substance and polymer in liquid propellant, from a feeder reservoir which optionally may be equipped with a cooling jacket.

The improved physical characteristics of the drug substance prepared according to the process of the present invention make them suitable for incorporation into in pharmaceutical formulations.

Accordingly, in a further aspect, the present invention provides for drug substance in crystalline form obtainable by a co-milling process as hereinbefore defined.

In a further aspect, the present invention provides for an intimate physical blend of drug substance and polymer obtainable by a co-milling process as hereinbefore defined.

The solid form of the drug substance obtainable by the process of the present invention may be presented in a variety of finished formulations, including for instance tablets, for example swallow tablets, dispersible tablets and chewable tablets; in capsules; aqueous syrups, sachets and for inhaler devices, including metered dose inhalers. These may be prepared by combining the drug substance of the present invention with excipients conventionally used in such formulations such as disintegrants, diluents, lubricants, wetting agents, binding agents, flavouring agents, sweeteners, colouring agents, preservatives, suspending agents, coating agents, pH modifiers and fillers, and further processing into finished formulations.

Thus, in a further aspect, the present invention provides for a pharmaceutical formulation which comprises a drug substance as hereinbefore defined optionally admixed with one or more pharmaceutically acceptable excipients.

Representative disintegrants for use in the present invention include maize starch and rice starch, cross-linked N-vinyl-2-pyrrolidinone, sodium starch glycollate, croscarmellose sodium, microcrystalline or microfine cellulose, low substituted hydroxypropyl cellulose, swellable ion exchange resins, formaldehyde-casein and alginates.

Representative lubricants for use in the present invention include a long chain fatty acid such as stearic acid, or salts thereof such as magnesium stearate.

Representative wetting agents include surfactants such as sodium lauryl sulphate, poloxamer, Tween 80 and Tween 20.

Representative pH modifiers for use in the present invention include citric acid, tartaric acid, maleic acid and sodium hydrogen carbonate.

Representative fillers for use in the present invention include silicon dioxide, mannitol, microcrystalline cellulose, dicalcium phosphate, lactose, sorbitol, calcium carbonate, magnesium carbonate, magnesium aluminium silicate, and maltodextrin.

The co-milling process of the present invention may be extended such that some or all of one or more of the aforementioned excipients are blended with the mixture of drug substance and polymer, prior to co-milling, and then co-milled with the drug substance and the polymers, to enhance the formulation properties of the drug substance, for instance processability.

Accordingly, in a further aspect, the present invention provides a process as hereinbefore defined and in which the drug substance and polymer are co-milled with one or more pharmaceutical excipients, for instance, one, two or three excipients.

Representative examples of excipients that may be included in the co-milling stage include a wetting agent such as sodium lauryl sulphate and/or a filler such as silicon dioxide, dicalcium phosphate, mannitol or lactose.

Drug substance prepared according to the present invention maybe characterised by a series of physical analytical techniques well known to those skilled in the art for analysing physical form, for instance XPRD, polarised light microscopy (PLM), thermal analysis, FT-IR and laser diffraction particle sizing.

All publications and references, including but not limited to patents and patent applications, cited in this specification are herein incorporated by reference in their entirety as if each publication or reference was specifically and individually indicated to be incorporated by reference herein as being fully set forth.

The invention will now be described by way of the following examples which do not limit the invention in any way.

EXAMPLES

Example 1

Model Compounds

Carbamazepine (form III, crystalline), dipyridamole (form II, crystalline), glibenclamide (crystalline) and indomethacin (γ form, crystalline) were milled in the absence and presence of propellant 134a, as neat drug substance and also with polyvinylpyrrolidone (PVP) and polyvinylpyrrolidone/vinyl acetate (PVP/VA) copolymer, according to the following method:

Method (a)—Conventional Milling 500 mg of drug or drug:polymer blend (PVP K30, PVP/VA 64 (BASF) and PVP/VA 37 (BASF)) (1:2 w/w) was ball milled in a mixer mill (MM2 Mixer mill, Glen Creston Ltd). The sample was milled at 17.5 1/sec in a 25 ml chamber for 120 minutes at 2% w/v with 2×12 mm diameter and 6×7 mm diameter stainless steel ball bearings.

(b) Milling with 1,1,1,2-tetrafluoroethane (134a)

500 mg of drug or drug:polymer blend (PVP K30) (1:2 w/w) was placed in a 25 ml milling chamber (2% w/v). Grinding media of 2×5 mm, 2×7 mm, 2×9 mm and 2×12 mm ball bearings were added. 10 g of 134a (Du Pont) was then added into the milling chamber via a valve. The sample was then milled for 2×20 minute periods at a frequency of 25 1/sec using a Retsch MM200 Mixer mill.

XPRD patterns of resultant products are shown as FIG. 1.1 to 1.4.

Results And Discussion 1.1 Carbamazepine

Conventional ball milling of carbamazepine resulted in conversion to a crystalline form, form III, irrespective of the starting material. Furthermore SEM analysis showed that carbamazepine formed strong secondary agglomerates as a result of the milling process, so that no significant decrease in particle size was observed.

Conventional ball milling of carbamazepine:PVP was found to result in amorphous conversion and a significant reduction in particle size compared to neat milled carbamazepine. In the presence of the PVP/VA 64 copolymer, there was partial retention of crystallinity whilst there appeared to be full retention with PVP/VA 37, this being attributed to a greater difference in solubility parameters between carbamazepine and the polymer/copolymers.

Carbamazepine milling with 134a resulted in complete conversion to a crystalline form, form III. Qualitative analysis of the of the XRPD diffractogram patterns suggested that the 134a milled product was more crystalline than the conventionally milled product. There was also a significant decrease in particle size, compared to conventionally milled material.

When carbamazepine:PVP was milled with 134a, carbamazepine retained its crystallinity.

1.2. Dipyridamole

Whilst conventional milling of dipyridamole led to the formation of predominantly amorphous product, milling with 134a resulted in dipyridamole form II (as judged by XRPD). Crystalline form was maintained for dipyrimadole:PVP 134a milled product. Particle sizing showed a significant decrease in size compared to conventionally milled product.

1.3. Glibenclamide

Conventional milling of glibenclamide resulted in an amorphous product. In comparison, glibenclamide milled in 134a remained in the same crystalline form as the starting material (by XRPD). This also resulted in a significant decrease in particle size, compared with conventional milling.

For glibenclamide:PVP 134a milled product, some crystalline form is present (XRPD). The particle size was significantly smaller than for conventionally milled product.

1.4. Indomethacin

Conventional milling of indomethacin resulted in a predominantly amorphous product. In comparison, XRPD and FT-IR analysis of 134a milled indomethacin showed that the process resulted in the drug being in the γ form. SEM analysis showed a significant decrease in particle size in comparison with conventionally milled indomethacin.

XRPD of the indomethacin:PVP 134a milled product also showed that it contained crystalline indomethacin, present in the γ form.

Dissolution Testing

The dissolution profiles of study compounds prepared by ball milling and 134a ball milling were measured according to the following method:

Method

Dissolution testing was carried out under sink conditions using a VanKel USP II dissolution apparatus (fluid pump Model 17-2300, water bath VK750D, water bath stirrer VK7010). Dissolution testing was carried out at 37.5° C.+/− 0.5° C. (Digitron Type K thermocouple thermometer). Vessels were stirred at 50 RPM. Samples underwent online UV analysis (Hewlett Packard 8453) at time points 0, 2, 5, 10, 15, 20, 30, 45 and 60 minutes. Samples were filtered with a 10 μm filters (Anachem). The pH 6.8 0.1M phosphate buffer[1] was degassed prior to commencement of the dissolution run (Copley Dissofill, model DSF2). Standard curves were prepared by dissolving drug in acetonitrile:water (1:1) for carbamazepine and glibenclamide or acetonitrile:pH 6.8 buffer (1:1) for dipyridamole and indomethacin. Drug concentration, UV cell path length, dissolution media and wavelength of detection were all compound specific. All analysis was carried out in triplicate.

[1] pH 6.8 buffer: 20 l prepared by addition of 10 l of $Na_2HPO_4.2H_2O$ 17.8 g/l to 10 l of $NaH_2PO_4.H_2O$ 13.8 g/l. pH was confirmed using a pH meter.

TABLE

Dissolution parameters used to analyse study compounds.

| Drug | Drug amount/ media volume | Dissolution media | UV wave-length (nm) | Cell path-length (mm) |
|---|---|---|---|---|
| Carbamazepine | 50 mg/900 ml | 0.1 M pH 6.8 phosphate buffer | 278-282 | 2 |
| Dipyridamole | 6 mg/500 ml | 0.1 M pH 6.8 phosphate buffer | 288-292 | 5 |
| Glibenclamide | 10 mg/900 ml | 1% SDS solution | 298-302 | 5 |
| Indomethacin | 50 mg/900 ml | 0.1 M pH 6.8 phosphate buffer | 262-266 | 2 |

Results

The results of the dissolution assay are shown in FIGS. 2.1 to 2.4. These showed a significant improvement in the dissolution rate for ball milled products. Further, these show that whilst ball milling neat drug in 134a led to a decrease in particle size, it resulted in an improved in dissolution rate for only dipyridamole. In comparison, when the milling was carried out with PVP in 134a, improved dissolution rates were observed for all.

Example 2

Co-Milling of Compound A with HMPCAS And HMPC

Compound A is 6-(4-chlorophenyl)-3-{4-[(3R)-3-hydroxypyrrolidin-1-yl]-3-methoxyphenyl}thieno[3,2-d]pyrimidin-4(3H)-one, the compound of formula:

(described in WO2005/042451 (Glaxo Group Limited), as Example 1).

Compound A (crystalline) was co-milled in the presence of propellant 134a, physically mixed and spray dried with the polymers hydroxypropyl methylcellulose (HPMC, Pharmcoat 603, Shin Etsu) and hydroxypropyl methylcellulose acetate succinate (HPMCAS, Aqoat-MG, Shin Etsu) according to the following methods:

Method (a) Co-Milling with 134a 500 mg of drug and 1 g of polymer (1:2 w/w) was placed in a 25 ml measuring chamber. Grinding media of 2 mm Yttrium-Zirconium beads (equivalent volume 5 ml) were added. 12 ml of propellant 134a was then added into the milling chamber via a valve. The sample was then milled for 30 minutes at a frequency of 25 1/sec using a Retsch MM200 Mixer mill.

(b) Physical Mix

Physical mixes of polymers and un-milled drug were also prepared by tumbling 500 g of drug and 1 g of polymer together in a glass jar.

(c) Spray Drying

Drug (2 g) and polymer (3 g) were dissolved in approximately 200 ml of dimethyl formamide and spray dried at approximately 2 ml/min using a lab scale spray drier (Buchi B191, outlet temperature about 95° C.). The spray dried powders were then further dried at 65° C. under vacuum for 48 hrs. The dispersions were amorphous by XRPD.

Figure 15:
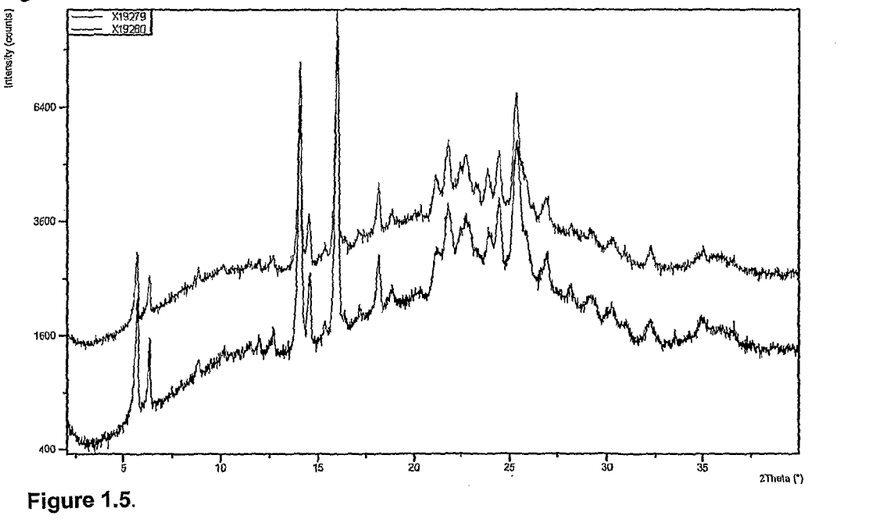
Figure 16:
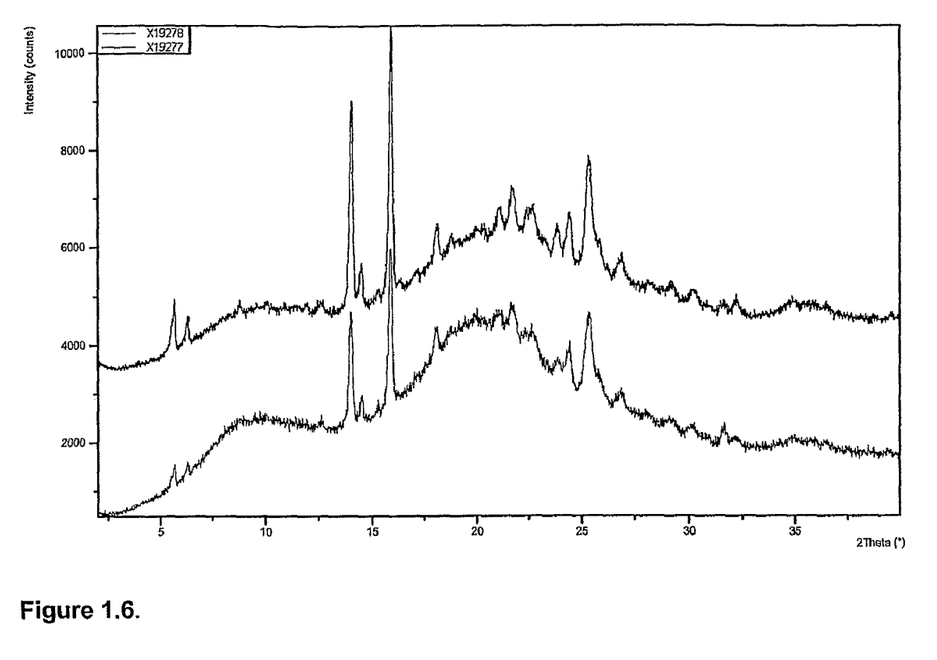
Figure 21:
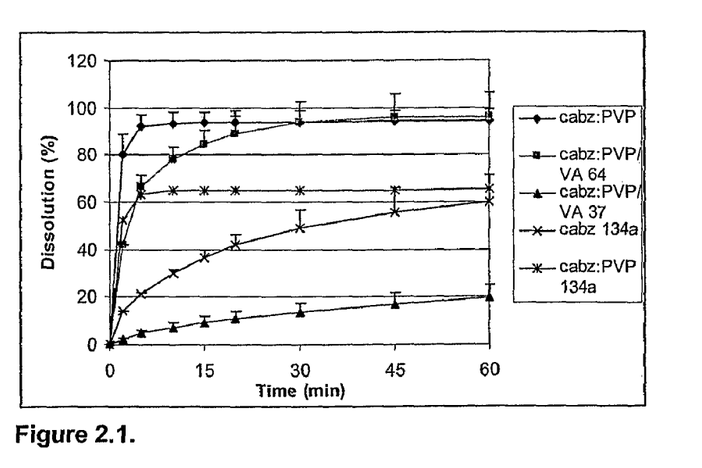
Figure 22:
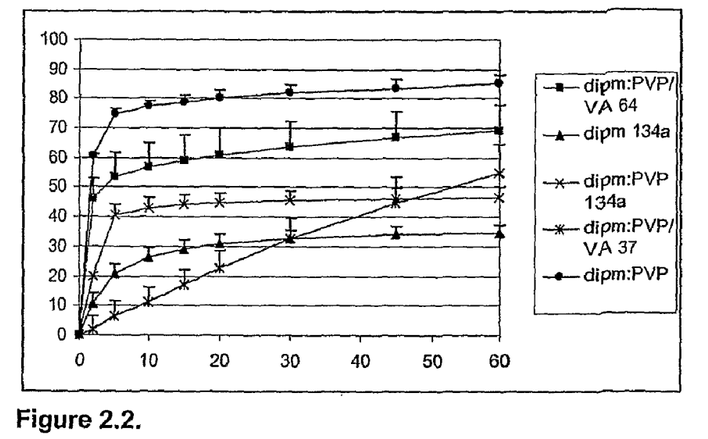
Figure 23:
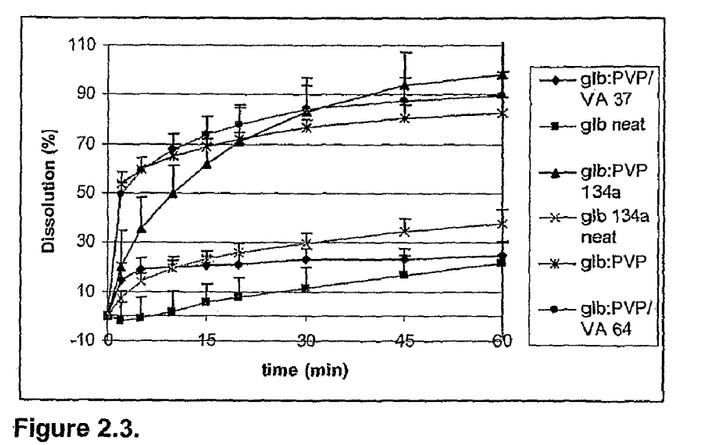
Figure 24:
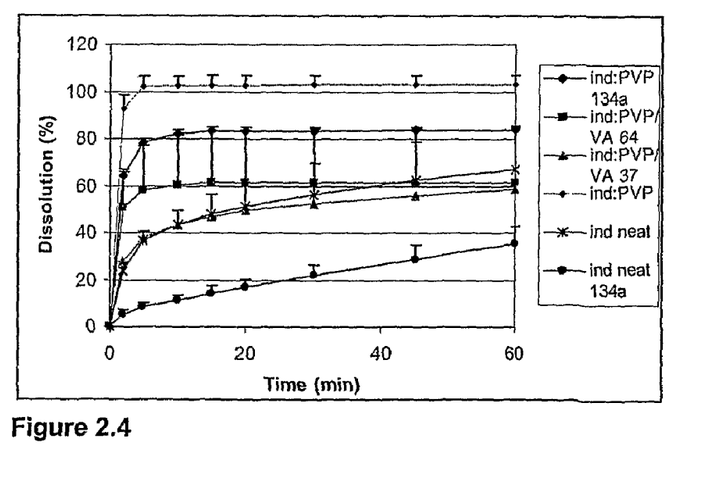

XRPD diffractograms of the 134a co-milled products and the comparative physical mixes are shown in FIG. 1.5 to 1.6. These show that the drug is present in the co-milled product substantially in a crystalline form. Thus, the co-milling process has not compromised the physical form of compound A.

Figure 25:
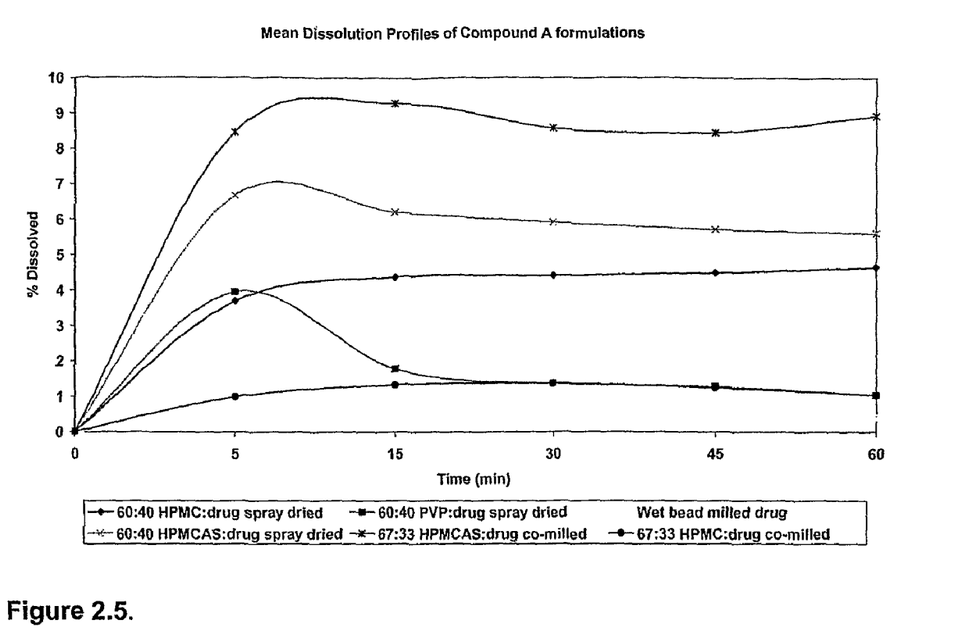

In addition, dissolution profiles of the spray dried and co-milled in 134a products, together with that for a conventional formulation of Compound A containing finely milled crystalline drug were obtained. A sample of the product (100 mg) in 0.01M hydrochloric acid was shaken for 5 min and then added to FaSSIF (Fasted State Simulated Intestinal Fluid, Galia et al, Pharmaceutical Research, 15, 698 to 705, 1998, 500 ml), at pH 6.5, in a USP2 bath, with a paddle speed of 50 rpm. Samples (2 ml) were taken after 15, 30, 45 and 60 min and then analysed by high pressure liquid chromatography (HPLC) for amount of Compound A. The results are presented in FIG. 2.5.

It is noted from the dissolution profile that the co-milled compound A with HPMCAS product, in which compound A is present in a crystalline form, shows a faster rate/greater extent of dissolution than the spray dried solid dispersion in which compound A is present in an amorphous form.

Example 3

Larger Scale Co-Milling

Figure 3:
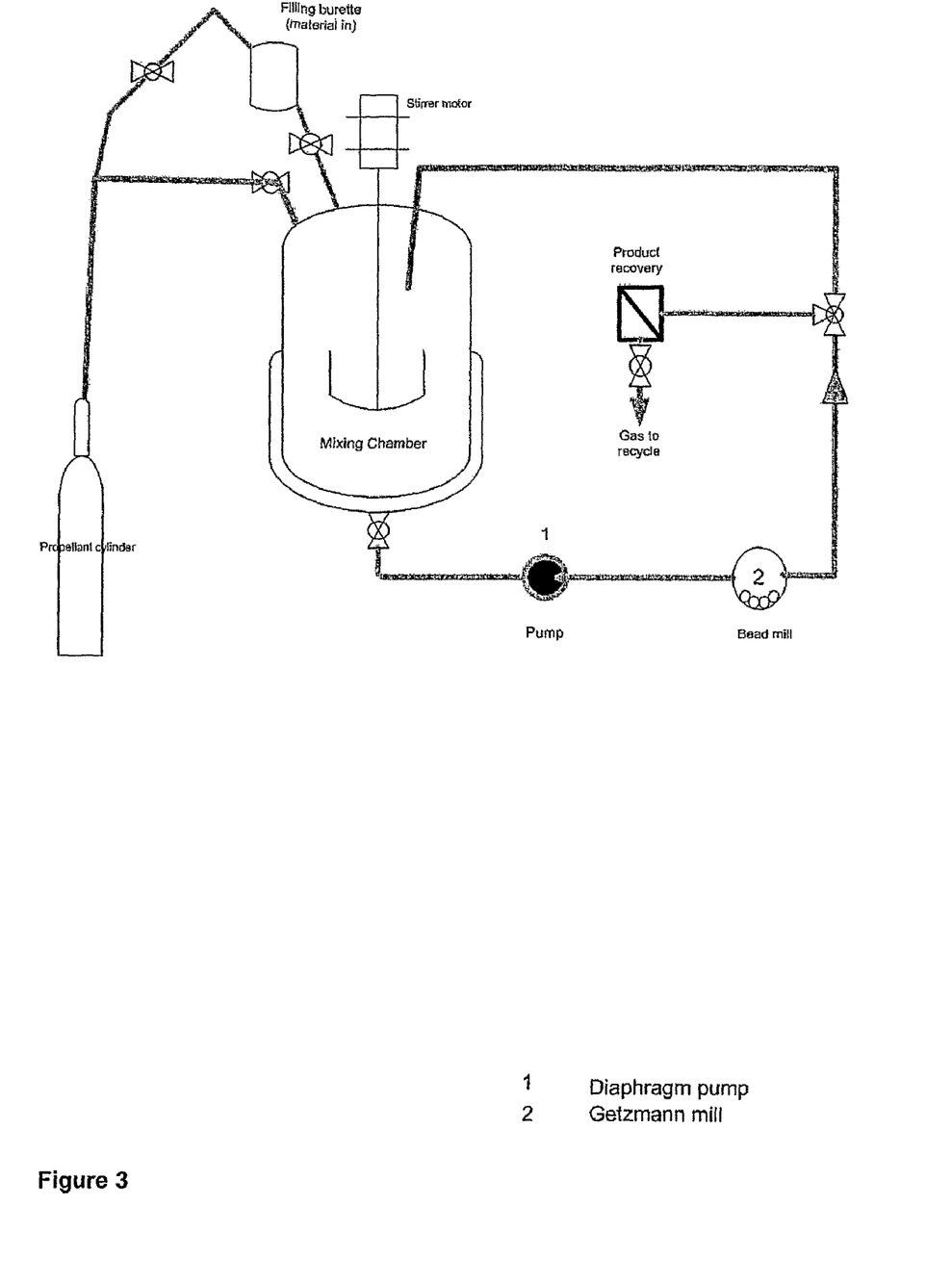
FIG. 3 shows larger scale bead milling equipment.
Figure 11:
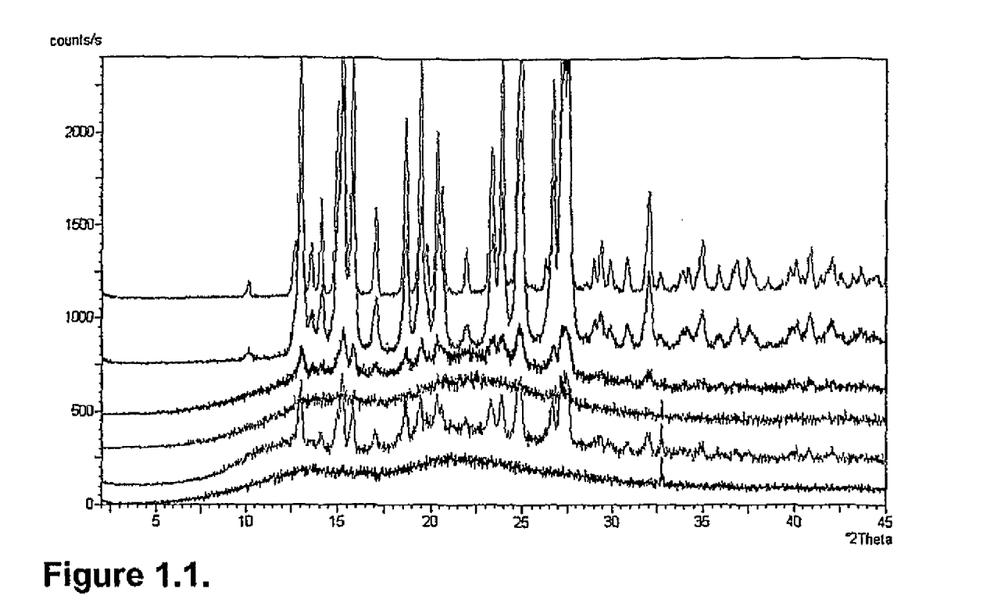
Figure 12:
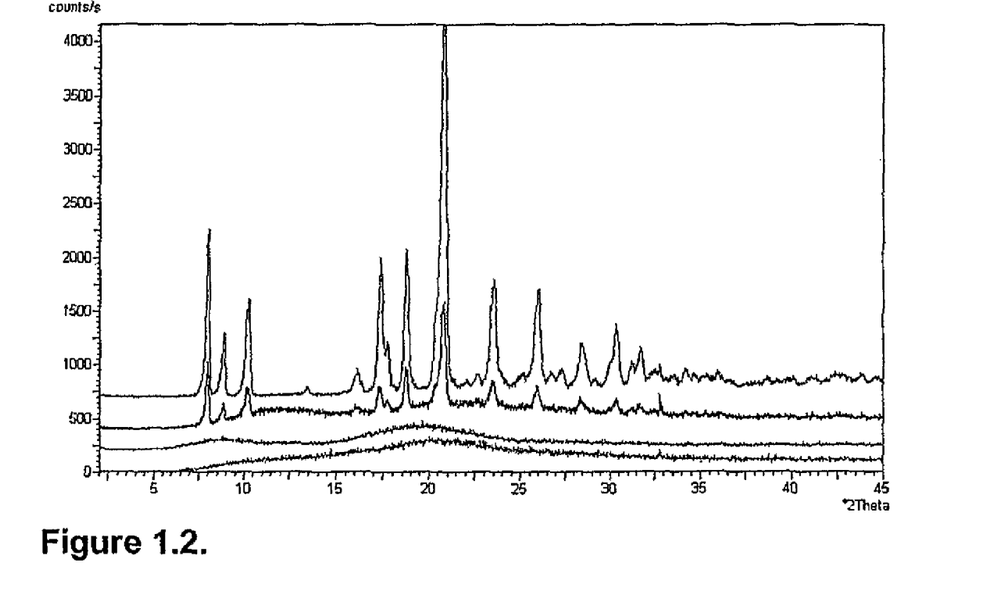
Figure 13:
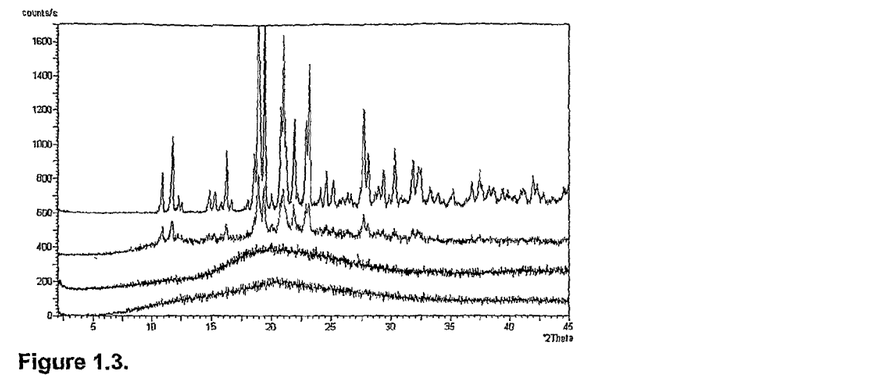
Figure 14:
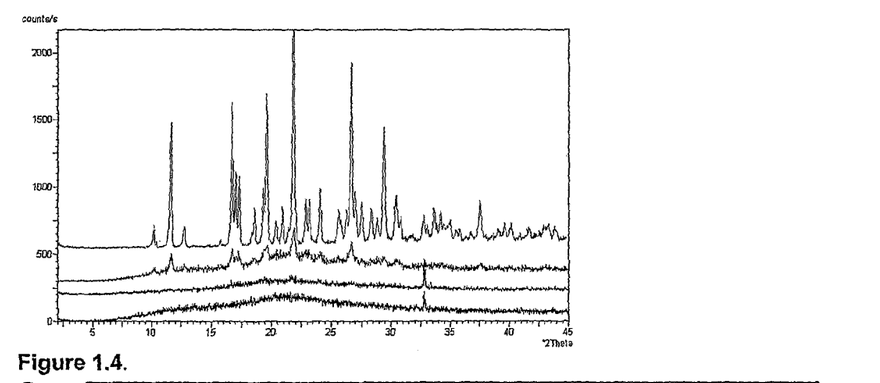

The set up shown in FIG. 3 may be used for larger scale co-milling. This comprises a mixing chamber into which drug substance and liquefied propellant (from compressed gas supply cylinder) are loaded. The resultant suspension is then circulated by a pump through a modified Getzmann SL-C_EX stirred media mill and back into the mixing chamber. Both the mill and the mixing chamber are cooled by Huber chillers. The whole system is rated to operate at 10 bar pressure. Normal operating pressure is 4-5 bar. The mill is capable of operating at scales of up to 5 kg, using media as small as 0.5 mm diameter. Assuming that the suspension being processed is approx 20% w/v, the system has a capacity of about 400 g (dictated by the capacity of the mixing vessel.

The capacity of the system may be increased by increasing the capacity of the product recovery system and the filling system.

The invention claimed is:

1. A process for preparing a solid form of a drug substance for use in a pharmaceutical formulation which process comprises co-milling a suspension of the drug substance and a pharmaceutically acceptable polymer which is hydroxypropylmethylcellulose succinate acetate in a liquid propellant.

2. A process as claimed in claim 1 in which drug substance and polymer are present in from 1 to 30% by weight of the liquid propellant.

3. A process as claimed in claim 2 in which drug substance and polymer are present in from 5 to 20% by weight of the liquid propellant.

4. A process as claimed in claim 2 in which the liquid propellant is 1,1,1,2-tetrafluoroethane.

5. A process as claimed in claim 1 in which the liquid propellant is 1,1,1,2-tetrafluoroethane.

6. A process as claimed in claim 1 in which the co-milling process is carried out at an operating pressure of up to 15 bar.

7. A process as claimed in claim 1 in which the drug substance and polymer are co-milled with one or more pharmaceutical excipients.

8. A process as claimed in claim 7 in which the liquid propellant is 1,1,1,2-tetrafluoroethane.

9. A process according to claim 1 which further comprises a second pharmaceutically acceptable polymer which is hydroxypropylmethylcellulose.

10. A process according to claim 9 wherein the ratio of drug:polymer is 2:1 to 1:10.

11. A process according to claim 10 wherein the ratio of drug:polymer is 2:1 to 1:5.

12. A process according to claim 1 wherein the ratio of drug:polymer is 2:1 to 1:10.

13. A process according to claim 12 wherein the ratio of drug:polymer is 2:1 to 1:5.

14. A process according to claim 1 wherein the drug substance and the polymer are blended prior to co-milling with one or more pharmaceutically acceptable excipients.

15. An intimate dispersion of the drug substance and polymer produced by the process according to claim 1.

16. A solid form of the drug substance produced by the process according to claim 1.

17. A pharmaceutical formulation comprising the solid form of the drug substance produced by the process according to claim 1 admixed with one or more pharmaceutically acceptable excipients.

18. A pharmaceutical formulation according to claim 17 wherein the one or more pharmaceutically acceptable excipient is selected from a the group consisting of disintegrant, diluent, lubricant, wetting agent, binding agent, flavouring agent, sweetener, colouring agent, preservative, suspending agent, coating agent, pH modifiers or filler.

* * * * *